United States Patent
Reya et al.

(10) Patent No.: US 6,465,249 B2
(45) Date of Patent: Oct. 15, 2002

(54) USE OF β-CATENIN IN THE EXPANSION OF STEM AND PROGENITOR CELLS

(75) Inventors: Tannishtha Reya, Mountain View; Roeland Nusse, Stanford; Irving L. Weissman, Redwood City, all of CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/766,387

(22) Filed: Jan. 18, 2001

(65) Prior Publication Data

US 2002/0004241 A1 Jan. 10, 2002

Related U.S. Application Data

(60) Provisional application No. 60/176,786, filed on Jan. 18, 2000.

(51) Int. Cl.[7] .............................. C12N 5/00; C12N 5/06; C12N 15/63; A01W 1/02; A61K 35/00
(52) U.S. Cl. ........................... 435/375; 435/2; 435/325; 435/363; 435/377; 435/455; 424/93.1; 424/93.21
(58) Field of Search ........................... 514/2, 44; 435/2, 435/325, 455, 363, 375, 377; 424/93.21

(56) References Cited

U.S. PATENT DOCUMENTS 5,652,122 A * 7/1997 Frankel et al. ............. 435/69.7
5,851,984 A * 12/1998 Matthews et al. ............. 514/2

OTHER PUBLICATIONS

L Hinck et al., Journal of Cell Biology, "Wnt–1 Modulates Cell–Cell Adhesion in Mammalian Cells by Stabilizing beta–Catenin Binding to the Cell Adhesion Protein Cadherin," Mar. 1994, vol. 124, No. 5, pp. 729–741.*

AJ Zhu et al., Development, "beta–catenin signalling modulates proliferative potential of human epidermal keratinocytes independently of intercellular adhesion," 1999, pp. 2285–2298.*

CS Young et al., Molecular and Cellular Biology, "Wnt–1 Induces Growth, Cytosolic beta–Catenin, and Tcf/Lef Transcriptional Activation in Rat–1 Fibroblasts," May 1998, vol. 18, No. 5, pp. 2474–2485.*

J Yang et al., Natl Library of Medicine, "The sub–cellular distribution of beta–catenin in the neural differentiation of RA induced P19 EC cells," Dec. 1998, 50(6): 671–8.*

Aberle et al. (1997) "β–catenin is a target for the ubiquitin0proteasome pathway." *The EMBO Journal*, vol. 16(13):3797–3804.

Domen et al. (1999) "Self–renewal, differentiation or death: regulation and manipulation of hematopoietic stem cell fate." *Molecular Medicine Today*, vol. 5:201–208.

Miyoshi et al. (1998) "Activation of the β–Catenin Gene in Pimary Hepatocellular Carcinomas by Somatic Alterations Involving Exon 3." *Cancer Research*, vol. 58:2524–2527.

(List continued on next page.)

*Primary Examiner*—James Ketter
*Assistant Examiner*—Qian J Li
(74) *Attorney, Agent, or Firm*—Pamela J. Sherwood; Bozicervic, Field & Francis LLP

(57) ABSTRACT

Mammalian progenitor or stem cells are expanded in vitro by increasing the levels of β-catenin in the cell. The expanded cells substantially maintain their original phenotype including the ability to give rise to multiple types of differentiated cells. The intracellular levels of β-catenin may be manipulated by providing exogenous β-catenin protein to the cell, or by introduction into the cell of a genetic construct encoding β-catenin. The β-catenin may be a wild-type or stabilized mutant form of the protein. Preferably the long term cell culture medium substantially lacks stromal cells and cytokines.

17 Claims, 3 Drawing Sheets

OTHER PUBLICATIONS

Morin et al. (1997) "Activation of β–Catenin–Tcf Signaling in Colon Cancer by Mutations in β–Catenin or APC." *Science*: 275:1787–1790.

Muller et al. (1998) "A β–catenin Mutation in a Sporadic Colorectal Tumor of the RER Phenotype and Absence of β–catenin Germline Mutations in FAP Patients." *Genes, Chromosomes & Cancer*, vol. 22:37–41.

Palacios et al. (1998) "Mutations in the β–catenin Gene (CTNNB1) in Endometrioid Ovarian Carcinomas." *Cancer Research*, vol. 58:1344–1347.

Voeller et al. (1998) "β–Catenin Mutations in Human Prostate Cancer." *Cancer Research*, vol. 58:2520–2523.

Ziegler et al. (1998) "Expansion of stem and progenitor cells." *Current Opinion in Hematology*, vol.. 5:434–440.

Zurawel et al. (1998) "Sporadic Medulloblastomas Contain Oncogenic β–Catenin Mutations." *Cancer Research*, vol. 58:896–899.

Chu et al. (1998), "Retrovirus–Mediated Gene Transfer into Human Hematopoietic Stem Cells." *J Mol Med*, vol. 76:184–192.

Damalas et al. (1999), "Excess Beta–Catenin Promotes Accumulation of Transcriptionally Active p53." *EMBO Journal*, vol. 18(11):3054–3063.

Satoh et al. (1998), "Successful Transfer of ADA Gene in vitro into Human Peripheral Blood $CD34^+$ Cells by Transfecting EBV–Based Episomal Vectors." *FEBS Letters*, vol. 441:39–42.

Zarrin et al. (1999), "Comparison of CMV, RSV, SV40 Viral and Vλ1 Cellular Promoters in B and T Lymphoid and Non–Lymphoid Cell Lines." *Biochemica et Biophysica Acta*, vol. 1446:135–139.

* cited by examiner

SEQUENCE LISTING

```
<160> NUMBER OF SEQ ID NOS:  4

<210> SEQ ID NO 1
<211> LENGTH: 3362
<212> TYPE: DNA
<213> ORGANISM: Homo sapiens
<220> FEATURE:
<221> NAME/KEY: CDS
<222> LOCATION: (215)...(2560)

<400> SEQUENCE: 1
aagcctctcg gtctgtggca gcagcgttgg cccggccccg ggagcggaga gcgaggggag        60
gcggagacgg aggaaggtct gaggagcagc ttcagtcccc gccgagccgc caccgcaggt       120
cgaggacggt cggactcccg cggcgggagg agcctgttcc cctgagggta tttgaagtat       180
accatacaac tgttttgaaa atccagcgtg gaca atg gct act caa gct gat ttg       235
                                    Met Ala Thr Gln Ala Asp Leu
                                     1               5 atg gag ttg gac atg gcc atg gaa cca gac aga aaa gcg gct gtt agt        283
Met Glu Leu Asp Met Ala Met Glu Pro Asp Arg Lys Ala Ala Val Ser
         10                  15                  20
```

-continued

```
cac tgg cag caa cag tct tac ctg gac tct gga atc cat tct ggt gcc      331
His Trp Gln Gln Gln Ser Tyr Leu Asp Ser Gly Ile His Ser Gly Ala
    25                  30                  35 act acc aca gct cct tct ctg agt ggt aaa ggc aat cct gag gaa gag      379
Thr Thr Thr Ala Pro Ser Leu Ser Gly Lys Gly Asn Pro Glu Glu Glu
 40                  45                  50                  55 gat gtg gat acc tcc caa gtc ctg tat gag tgg gaa cag gga ttt tct      427
Asp Val Asp Thr Ser Gln Val Leu Tyr Glu Trp Glu Gln Gly Phe Ser
                     60                  65                  70 cag tcc ttc act caa gaa caa gta gct gat att gat gga cag tat gca      475
Gln Ser Phe Thr Gln Glu Gln Val Ala Asp Ile Asp Gly Gln Tyr Ala
                75                  80                  85 atg act cga gct cag agg gta cga gct gct atg ttc cct gag aca tta      523
Met Thr Arg Ala Gln Arg Val Arg Ala Ala Met Phe Pro Glu Thr Leu
            90                  95                 100 gat gag ggc atg cag atc cca tct aca cag ttt gat gct gct cat ccc      571
Asp Glu Gly Met Gln Ile Pro Ser Thr Gln Phe Asp Ala Ala His Pro
        105                 110                 115 act aat gtc cag cgt ttg gct gaa cca tca cag atg ctg aaa cat gca      619
Thr Asn Val Gln Arg Leu Ala Glu Pro Ser Gln Met Leu Lys His Ala
120                 125                 130                 135 gtt gta aac ttg att aac tat caa gat gat gca gaa ctt gcc aca cgt      667
Val Val Asn Leu Ile Asn Tyr Gln Asp Asp Ala Glu Leu Ala Thr Arg
                140                 145                 150 gca atc cct gaa ctg aca aaa ctg cta aat gac gag gac cag gtg gtg      715
Ala Ile Pro Glu Leu Thr Lys Leu Leu Asn Asp Glu Asp Gln Val Val
            155                 160                 165 gtt aat aag gct gca gtt atg gtc cat cag ctt tct aaa aag gaa gct      763
Val Asn Lys Ala Ala Val Met Val His Gln Leu Ser Lys Lys Glu Ala
        170                 175                 180 tcc aga cac gct atc atg cgt tct cct cag atg gtg tct gct att gta      811
Ser Arg His Ala Ile Met Arg Ser Pro Gln Met Val Ser Ala Ile Val
185                 190                 195 cgt acc atg cag aat aca aat gat gta gaa aca gct cgt tgt acc gct      859
Arg Thr Met Gln Asn Thr Asn Asp Val Glu Thr Ala Arg Cys Thr Ala
200                 205                 210                 215 ggg acc ttg cat aac ctt tcc cat cat cgt gag ggc tta ctg gcc atc      907
Gly Thr Leu His Asn Leu Ser His His Arg Glu Gly Leu Leu Ala Ile
                220                 225                 230 ttt aag tct gga ggc att cct gcc ctg gtg aaa atg ctt ggt tca cca      955
Phe Lys Ser Gly Gly Ile Pro Ala Leu Val Lys Met Leu Gly Ser Pro
            235                 240                 245 gtg gat tct gtg ttg ttt tat gcc att aca act ctc cac aac ctt tta      1003
Val Asp Ser Val Leu Phe Tyr Ala Ile Thr Thr Leu His Asn Leu Leu
        250                 255                 260 tta cat caa gaa gga gct aaa atg gca gtg cgt tta gct ggt ggg ctg      1051
Leu His Gln Glu Gly Ala Lys Met Ala Val Arg Leu Ala Gly Gly Leu
265                 270                 275 cag aaa atg gtt gcc ttg ctc aac aaa aca aat gtt aaa ttc ttg gct      1099
Gln Lys Met Val Ala Leu Leu Asn Lys Thr Asn Val Lys Phe Leu Ala
280                 285                 290                 295 att acg aca gac tgc ctt caa att tta gct tat ggc aac caa gaa agc      1147
Ile Thr Thr Asp Cys Leu Gln Ile Leu Ala Tyr Gly Asn Gln Glu Ser
                300                 305                 310 aag ctc atc ata ctg gct agt ggt gga ccc caa gct tta gta aat ata      1195
Lys Leu Ile Ile Leu Ala Ser Gly Gly Pro Gln Ala Leu Val Asn Ile
            315                 320                 325 atg agg acc tat act tac gaa aaa cta ctg tgg acc aca agc aga gtg      1243
Met Arg Thr Tyr Thr Tyr Glu Lys Leu Leu Trp Thr Thr Ser Arg Val
        330                 335                 340
```

-continued

```
ctg aag gtg cta tct gtc tgc tct agt aat aag ccg gct att gta gaa    1291
Leu Lys Val Leu Ser Val Cys Ser Ser Asn Lys Pro Ala Ile Val Glu
    345                 350                 355 gct ggt gga atg caa gct tta gga ctt cac ctg aca gat cca agt caa    1339
Ala Gly Gly Met Gln Ala Leu Gly Leu His Leu Thr Asp Pro Ser Gln
360                 365                 370                 375 cgt ctt gtt cag aac tgt ctt tgg act ctc agg aat ctt tca gat gct    1387
Arg Leu Val Gln Asn Cys Leu Trp Thr Leu Arg Asn Leu Ser Asp Ala
                380                 385                 390 gca act aaa cag gaa ggg atg gaa ggt ctc ctt ggg act ctt gtt cag    1435
Ala Thr Lys Gln Glu Gly Met Glu Gly Leu Leu Gly Thr Leu Val Gln
            395                 400                 405 ctt ctg ggt tca gat gat ata aat gtg gtc acc tgt gca gct gga att    1483
Leu Leu Gly Ser Asp Asp Ile Asn Val Val Thr Cys Ala Ala Gly Ile
        410                 415                 420 ctt tct aac ctc act tgc aat aat tat aag aac aag atg atg gtc tgc    1531
Leu Ser Asn Leu Thr Cys Asn Asn Tyr Lys Asn Lys Met Met Val Cys
    425                 430                 435 caa gtg ggt ggt ata gag gct ctt gtg cgt act gtc ctt cgg gct ggt    1579
Gln Val Gly Gly Ile Glu Ala Leu Val Arg Thr Val Leu Arg Ala Gly
440                 445                 450                 455 gac agg gaa gac atc act gag cct gcc atc tgt gct ctt cgt cat ctg    1627
Asp Arg Glu Asp Ile Thr Glu Pro Ala Ile Cys Ala Leu Arg His Leu
                460                 465                 470 acc agc cga cac caa gaa gca gag atg gcc cag aat gca gtt cgc ctt    1675
Thr Ser Arg His Gln Glu Ala Glu Met Ala Gln Asn Ala Val Arg Leu
            475                 480                 485 cac tat gga cta cca gtt gtg gtt aag ctc tta cac cca cca tcc cac    1723
His Tyr Gly Leu Pro Val Val Val Lys Leu Leu His Pro Pro Ser His
        490                 495                 500 tgg cct ctg ata aag gct act gtt gga ttg att cga aat ctt gcc ctt    1771
Trp Pro Leu Ile Lys Ala Thr Val Gly Leu Ile Arg Asn Leu Ala Leu
    505                 510                 515 tgt ccc gca aat cat gca cct ttg cgt gag cag ggt gcc att cca cga    1819
Cys Pro Ala Asn His Ala Pro Leu Arg Glu Gln Gly Ala Ile Pro Arg
520                 525                 530                 535 cta gtt cag ttg ctt gtt cgt gca cat cag gat acc cag cgc cgt acg    1867
Leu Val Gln Leu Leu Val Arg Ala His Gln Asp Thr Gln Arg Arg Thr
                540                 545                 550 tcc atg ggt ggg aca cag cag caa ttt gtg gag ggg gtc cgc atg gaa    1915
Ser Met Gly Gly Thr Gln Gln Gln Phe Val Glu Gly Val Arg Met Glu
            555                 560                 565 gaa ata gtt gaa ggt tgt acc gga gcc ctt cac atc cta gct cgg gat    1963
Glu Ile Val Glu Gly Cys Thr Gly Ala Leu His Ile Leu Ala Arg Asp
        570                 575                 580 gtt cac aac cga att gtt atc aga gga cta aat acc att cca ttg ttt    2011
Val His Asn Arg Ile Val Ile Arg Gly Leu Asn Thr Ile Pro Leu Phe
    585                 590                 595 gtg cag ctg ctt tat tct ccc att gaa aac atc caa aga gta gct gca    2059
Val Gln Leu Leu Tyr Ser Pro Ile Glu Asn Ile Gln Arg Val Ala Ala
600                 605                 610                 615 ggg gtc ctc tgt gaa ctt gct cag gac aag gaa gct gca gaa gct att    2107
Gly Val Leu Cys Glu Leu Ala Gln Asp Lys Glu Ala Ala Glu Ala Ile
                620                 625                 630 gaa gct gag gga gcc aca gct cct ctg aca gag tta ctt cac tct agg    2155
Glu Ala Glu Gly Ala Thr Ala Pro Leu Thr Glu Leu Leu His Ser Arg
            635                 640                 645 aat gaa ggt gtg gcg aca tat gca gct gct gtt ttg ttc cga atg tct    2203
Asn Glu Gly Val Ala Thr Tyr Ala Ala Ala Val Leu Phe Arg Met Ser
        650                 655                 660
```

-continued

| | |
|---|---|
| gag gac aag cca caa gat tac aag aaa cgg ctt tca gtt gag ctg acc<br>Glu Asp Lys Pro Gln Asp Tyr Lys Lys Arg Leu Ser Val Glu Leu Thr<br>665                    670                    675 | 2251 |
| agc tct ctc ttc aga aca gag cca atg gct tgg aat gag act gct gat<br>Ser Ser Leu Phe Arg Thr Glu Pro Met Ala Trp Asn Glu Thr Ala Asp<br>680                    685                    690                    695 | 2299 |
| ctt gga ctt gat att ggt gcc cag gga gaa ccc ctt gga tat cgc cag<br>Leu Gly Leu Asp Ile Gly Ala Gln Gly Glu Pro Leu Gly Tyr Arg Gln<br>                    700                    705                    710 | 2347 |
| gat gat cct agc tat cgt tct ttt cac tct ggt gga tat ggc cag gat<br>Asp Asp Pro Ser Tyr Arg Ser Phe His Ser Gly Gly Tyr Gly Gln Asp<br>715                    720                    725 | 2395 |
| gcc ttg ggt atg gac ccc atg atg gaa cat gag atg ggt ggc cac cac<br>Ala Leu Gly Met Asp Pro Met Met Glu His Glu Met Gly Gly His His<br>730                    735                    740 | 2443 |
| cct ggt gct gac tat cca gtt gat ggg ctg cca gat ctg ggg cat gcc<br>Pro Gly Ala Asp Tyr Pro Val Asp Gly Leu Pro Asp Leu Gly His Ala<br>745                    750                    755 | 2491 |
| cag gac ctc atg gat ggg ctg cct cca ggt gac agc aat cag ctg gcc<br>Gln Asp Leu Met Asp Gly Leu Pro Pro Gly Asp Ser Asn Gln Leu Ala<br>760                    765                    770                    775 | 2539 |
| tgg ttt gat act gac ctg taa atcatccttt agctgtattg tctgaacttg<br>Trp Phe Asp Thr Asp Leu  *<br>                  780 | 2590 |
| cattgtgatt ggcctgtaga gttgctgaga gggctcgagg ggtgggctgg tatctcagaa | 2650 |
| agtgcctgac acactaacca agctgagttt cctatgggaa caattgaagt aaacttttg | 2710 |
| ttctggtcct ttttggtcga ggagtaacaa tacaaatgga ttttgggagt gactcaagaa | 2770 |
| gtgaagaatg cacaagaatg gatcacaaga tggaatttag caaaccctag ccttgcttgt | 2830 |
| taaaattttt tttttttttt ttttaagaat atctgtaatg gtactgactt tgcttgcttt | 2890 |
| gaagtagctc tttttttttt tttttttttt ttttttttgca gtaactgttt tttaagtctc | 2950 |
| tcgtagtgtt aagttatagt gaatactgct acagcaattt ctaattttta agaattgagt | 3010 |
| aatggtgtag aacactaatt aattcataat cactctaatt aattgtaatc tgaataaagt | 3070 |
| gtaacaattg tgtagccttt ttgtataaaa tagacaaata gaaaatggtc caattagttt | 3130 |
| cctttttaat atgcttaaaa taagcaggtg gatctatttc atgttttttga tcaaaaacta | 3190 |
| tttgggatat gtatgggtag ggtaaatcag taagaggtgt tatttggaac cttgttttgg | 3250 |
| acagtttacc agttgccttt tatcccaaag ttgttgtaac ctgctgtgat acgatgcttc | 3310 |
| aagagaaaat gcggttataa aaaatggttc agaattaaac ttttaattca tt | 3362 |

<210> SEQ ID NO 2
<211> LENGTH: 781
<212> TYPE: PRT
<213> ORGANISM: Homo sapiens

<400> SEQUENCE: 2

Met Ala Thr Gln Ala Asp Leu Met Glu Leu Asp Met Ala Met Glu Pro
1                  5                      10                      15

Asp Arg Lys Ala Ala Val Ser His Trp Gln Gln Gln Ser Tyr Leu Asp
                    20                      25                      30

Ser Gly Ile His Ser Gly Ala Thr Thr Thr Ala Pro Ser Leu Ser Gly
                35                      40                      45

Lys Gly Asn Pro Glu Glu Glu Asp Val Asp Thr Ser Gln Val Leu Tyr
  50                      55                      60

-continued

```
Glu Trp Glu Gln Gly Phe Ser Gln Ser Phe Thr Gln Glu Gln Val Ala
 65                  70                  75                  80

Asp Ile Asp Gly Gln Tyr Ala Met Thr Arg Ala Gln Arg Val Arg Ala
                 85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480
```

```
Ala Gln Asn Ala Val Arg Leu His Tyr Gly Leu Pro Val Val Lys
            485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
            530                 535                 540

Gln Asp Thr Gln Arg Arg Thr Ser Met Gly Thr Gln Gln Phe
545                 550                 555                 560

Val Glu Gly Val Arg Met Glu Ile Val Glu Gly Cys Thr Gly Ala
            565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
            610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
            645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
            675                 680                 685

Ala Trp Asn Glu Thr Ala Asp Leu Gly Leu Asp Ile Gly Ala Gln Gly
            690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
            725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
            770                 775                 780

<210> SEQ ID NO 3
<211> LENGTH: 2702
<212> TYPE: DNA
<213> ORGANISM: Mus musculus
<220> FEATURE:
<221> NAME/KEY: CDS
<222> LOCATION: (98)...(2443)

<400> SEQUENCE: 3
gaattccgag cgtcagtgca ggaggccgat tccgagcggg cggccgcgag gtaggtgaag      60
ctcagcgcag agctgctgtg acaccgctgc gtggaca atg gct act caa gct gac     115
                                          Met Ala Thr Gln Ala Asp
                                            1               5 ctg atg gag ttg gac atg gcc atg gag ccg gac aga aaa gct gct gtc     163
Leu Met Glu Leu Asp Met Ala Met Glu Pro Asp Arg Lys Ala Ala Val
            10                  15                  20
```

-continued

| | |
|---|---|
| agc cac tgg cag cag cag tct tac ttg gat tct gga atc cat tct ggt<br>Ser His Trp Gln Gln Gln Ser Tyr Leu Asp Ser Gly Ile His Ser Gly<br>        25                        30                      35 | 211 |
| gcc acc acc aca gct cct tcc ctg agt ggc aag ggc aac cct gag gaa<br>Ala Thr Thr Thr Ala Pro Ser Leu Ser Gly Lys Gly Asn Pro Glu Glu<br>40                        45                        50 | 259 |
| gaa gat gtt gac acc tcc caa gtc ctt tat gaa tgg gag caa ggc ttt<br>Glu Asp Val Asp Thr Ser Gln Val Leu Tyr Glu Trp Glu Gln Gly Phe<br>55                        60                        65                      70 | 307 |
| tcc cag tcc ttc acg caa gag caa gta gct gat att gac ggg cag tat<br>Ser Gln Ser Phe Thr Gln Glu Gln Val Ala Asp Ile Asp Gly Gln Tyr<br>                  75                        80                        85 | 355 |
| gca atg act agg gct cag agg gtc cga gct gcc atg ttc cct gag acg<br>Ala Met Thr Arg Ala Gln Arg Val Arg Ala Ala Met Phe Pro Glu Thr<br>90                        95                        100 | 403 |
| cta gat gag ggc atg cag atc cca tcc acg cag ttt gac gct gct cat<br>Leu Asp Glu Gly Met Gln Ile Pro Ser Thr Gln Phe Asp Ala Ala His<br>                  105                       110                   115 | 451 |
| ccc act aat gtc cag cgc ttg gct gaa cca tca cag atg ttg aaa cat<br>Pro Thr Asn Val Gln Arg Leu Ala Glu Pro Ser Gln Met Leu Lys His<br>120                       125                       130 | 499 |
| gca gtc gtc aat ttg att aac tat cag gat gac gcg gaa ctt gcc aca<br>Ala Val Val Asn Leu Ile Asn Tyr Gln Asp Asp Ala Glu Leu Ala Thr<br>135                       140                       145                   150 | 547 |
| cgt gca att cct gag ctg aca aaa ctg cta aac gat gag gac cag gtg<br>Arg Ala Ile Pro Glu Leu Thr Lys Leu Leu Asn Asp Glu Asp Gln Val<br>                  155                       160                   165 | 595 |
| gta gtt aat aaa gct gct gtt atg gtc cat cag ctt tcc aaa aag gaa<br>Val Val Asn Lys Ala Ala Val Met Val His Gln Leu Ser Lys Lys Glu<br>170                       175                       180 | 643 |
| gct tcc aga cat gcc atc atg cgc tcc cct cag atg gtg tct gcc att<br>Ala Ser Arg His Ala Ile Met Arg Ser Pro Gln Met Val Ser Ala Ile<br>185                       190                       195 | 691 |
| gta cgc acc atg cag aat aca aat gat gta gag aca gct cgt tgt act<br>Val Arg Thr Met Gln Asn Thr Asn Asp Val Glu Thr Ala Arg Cys Thr<br>                  200                       205                   210 | 739 |
| gct ggg acc ctt cac aac ctt tct cac cac cgc gag ggc ttg ctg gcc<br>Ala Gly Thr Leu His Asn Leu Ser His His Arg Glu Gly Leu Leu Ala<br>215                       220                       225                   230 | 787 |
| atc ttt aag tct ggt ggc atc cca gcg ctg gtg aaa atg ctt ggg tca<br>Ile Phe Lys Ser Gly Gly Ile Pro Ala Leu Val Lys Met Leu Gly Ser<br>                  235                       240                   245 | 835 |
| cca gtg gat tct gta ctg ttc tac gcc atc acg aca ctg cat aat ctc<br>Pro Val Asp Ser Val Leu Phe Tyr Ala Ile Thr Thr Leu His Asn Leu<br>250                       255                       260 | 883 |
| ctg ctc cat cag gaa gga gct aaa atg gca gtg cgc cta gct ggt gga<br>Leu Leu His Gln Glu Gly Ala Lys Met Ala Val Arg Leu Ala Gly Gly<br>                  265                       270                   275 | 931 |
| ctg cag aaa atg gtt gct ttg ctc aac aaa aca aac gtg aaa ttc ttg<br>Leu Gln Lys Met Val Ala Leu Leu Asn Lys Thr Asn Val Lys Phe Leu<br>280                       285                       290 | 979 |
| gct att aca aca gac tgc ctt cag atc tta gct tat ggc aat caa gag<br>Ala Ile Thr Thr Asp Cys Leu Gln Ile Leu Ala Tyr Gly Asn Gln Glu<br>295                       300                       305                   310 | 1027 |
| agc aag ctc atc att ctg gcc agt ggt gga ccc caa gcc tta gta aac<br>Ser Lys Leu Ile Ile Leu Ala Ser Gly Gly Pro Gln Ala Leu Val Asn<br>                  315                       320                   325 | 1075 |
| ata atg agg acc tac act tat gag aag ctt ctg tgg acc aca agc aga<br>Ile Met Arg Thr Tyr Thr Tyr Glu Lys Leu Leu Trp Thr Thr Ser Arg<br>330                       335                       340 | 1123 |

-continued

| | | |
|---|---|---|
| gtg ctg aaa gtg ctg tct gtc tgc tct agc aac aag ccg gcc att gta<br>Val Leu Lys Val Leu Ser Val Cys Ser Ser Asn Lys Pro Ala Ile Val<br>         345                   350                   355 | 1171 |
| gaa gct ggt ggg atg cag gca ctg ggg ctt cat ctg aca gac cca agt<br>Glu Ala Gly Gly Met Gln Ala Leu Gly Leu His Leu Thr Asp Pro Ser<br>360                   365                   370 | 1219 |
| cag cga ctt gtt caa aac tgt ctt tgg act ctc aga aac ctt tca gat<br>Gln Arg Leu Val Gln Asn Cys Leu Trp Thr Leu Arg Asn Leu Ser Asp<br>375                  380                 385                 390 | 1267 |
| gca gcg act aag cag gaa ggg atg gaa ggc ctc ctt ggg act cta gtg<br>Ala Ala Thr Lys Gln Glu Gly Met Glu Gly Leu Leu Gly Thr Leu Val<br>                   395                   400                   405 | 1315 |
| cag ctt ctg ggt tcc gat gat ata aat gtg gtc acc tgt gca gct gga<br>Gln Leu Leu Gly Ser Asp Asp Ile Asn Val Val Thr Cys Ala Ala Gly<br>                 410                   415                 420 | 1363 |
| att ctc tct aac ctc act tgc aat aat tac aaa aac aag atg atg gtg<br>Ile Leu Ser Asn Leu Thr Cys Asn Asn Tyr Lys Asn Lys Met Met Val<br>425                  430                 435 | 1411 |
| tgc caa gtg ggt ggc ata gag gct ctt gta cgc acc gtc ctt cgt gct<br>Cys Gln Val Gly Gly Ile Glu Ala Leu Val Arg Thr Val Leu Arg Ala<br>         440                   445                 450 | 1459 |
| ggt gac agg gaa gac atc act gag cct gcc atc tgt gct ctt cgt cat<br>Gly Asp Arg Glu Asp Ile Thr Glu Pro Ala Ile Cys Ala Leu Arg His<br>455                  460                 465                 470 | 1507 |
| ctg acc agc cgg cat cag gaa gcc gag atg gcc cag aat gcc gtt cgc<br>Leu Thr Ser Arg His Gln Glu Ala Glu Met Ala Gln Asn Ala Val Arg<br>                   475                   480                   485 | 1555 |
| ctt cat tat gga ctg cct gtt gtg gtt aaa ctc ctg cac cca cca tcc<br>Leu His Tyr Gly Leu Pro Val Val Val Lys Leu Leu His Pro Pro Ser<br>                 490                   495                 500 | 1603 |
| cac tgg cct ctg ata aag gca act gtt gga ttg att cga aac ctt gcc<br>His Trp Pro Leu Ile Lys Ala Thr Val Gly Leu Ile Arg Asn Leu Ala<br>505                 510                 515 | 1651 |
| ctt tgc cca gca aat cat gcg cct ttg cgg gaa cag ggt gct att cca<br>Leu Cys Pro Ala Asn His Ala Pro Leu Arg Glu Gln Gly Ala Ile Pro<br>520                  525                 530 | 1699 |
| cga cta gtt cag ctg ctt gta cga gca cat cag gac acc caa cgg cgc<br>Arg Leu Val Gln Leu Leu Val Arg Ala His Gln Asp Thr Gln Arg Arg<br>535                 540                 545                 550 | 1747 |
| acc tcc atg ggt gga acg cag cag cag ttt gtg gag ggc gtg cgc atg<br>Thr Ser Met Gly Gly Thr Gln Gln Gln Phe Val Glu Gly Val Arg Met<br>                 555                   560                 565 | 1795 |
| gag gaa ata gtc gaa ggg tgt act gga gct ctc cac atc ctt gct cgg<br>Glu Glu Ile Val Glu Gly Cys Thr Gly Ala Leu His Ile Leu Ala Arg<br>                 570                   575                 580 | 1843 |
| gac gtt cac aac cgg att gta atc cga gga ctc aat acc att cca ttg<br>Asp Val His Asn Arg Ile Val Ile Arg Gly Leu Asn Thr Ile Pro Leu<br>         585                   590                 595 | 1891 |
| ttt gtg cag ttg ctt tat tct ccc att gaa aat atc caa aga gta gct<br>Phe Val Gln Leu Leu Tyr Ser Pro Ile Glu Asn Ile Gln Arg Val Ala<br>600                 605                 610 | 1939 |
| gca ggg gtc ctc tgt gaa ctt gct cag gac aag gag gct gca gag gcc<br>Ala Gly Val Leu Cys Glu Leu Ala Gln Asp Lys Glu Ala Ala Glu Ala<br>615                 620                 625                 630 | 1987 |
| att gaa gct gag gga gcc aca gct ccc ctg aca gag tta ctc cac tcc<br>Ile Glu Ala Glu Gly Ala Thr Ala Pro Leu Thr Glu Leu Leu His Ser<br>                 635                   640                 645 | 2035 |
| agg aat gaa ggc gtg gca aca tac gca gct gct gtc cta ttc cga atg<br>Arg Asn Glu Gly Val Ala Thr Tyr Ala Ala Ala Val Leu Phe Arg Met<br>         650                   655                 660 | 2083 |

```
tct gag gac aag cca cag gat tac aag aag cgg ctt tca gtc gag ctg       2131
Ser Glu Asp Lys Pro Gln Asp Tyr Lys Lys Arg Leu Ser Val Glu Leu
            665                 670                 675 acc agt tcc ctc ttc agg aca gag cca atg gct tgg aat gag act gca       2179
Thr Ser Ser Leu Phe Arg Thr Glu Pro Met Ala Trp Asn Glu Thr Ala
    680                 685                 690 gat ctt gga ctg gac att ggt gcc cag gga gaa gcc ctt gga tat cgc       2227
Asp Leu Gly Leu Asp Ile Gly Ala Gln Gly Glu Ala Leu Gly Tyr Arg
695                 700                 705                 710 cag gat gat ccc agc tac cgt tct ttt cac tct ggt gga tac ggc cag       2275
Gln Asp Asp Pro Ser Tyr Arg Ser Phe His Ser Gly Gly Tyr Gly Gln
            715                 720                 725 gat gcc ttg ggg atg gac cct atg atg gag cat gag atg ggt ggc cac       2323
Asp Ala Leu Gly Met Asp Pro Met Met Glu His Glu Met Gly Gly His
                730                 735                 740 cac cct ggt gct gac tat cca gtt gat ggg ctg cct gat ctg gga cac       2371
His Pro Gly Ala Asp Tyr Pro Val Asp Gly Leu Pro Asp Leu Gly His
            745                 750                 755 gcc cag gac ctc atg gat ggg ctg ccc cca ggt gat agc aat cag ctg       2419
Ala Gln Asp Leu Met Asp Gly Leu Pro Pro Gly Asp Ser Asn Gln Leu
        760                 765                 770 gcc tgg ttt gat act gac ctg taa atcgtcctta gtaagaaagc ttataaaagc      2473
Ala Trp Phe Asp Thr Asp Leu  *
775                 780 cagtgtgggt gaatacttac tctgcctgca gaactccaga aagacttggt agggtgggaa     2533
tggttttagg cctgtttgta aatctgccac caaacagata cataccttgg aaggagatgt     2593
tcatgtgtgg aagtttctca cgttgatgtt tttgccacag cttttgcagc gttatactca     2653
gatgagtaac atttgctgtt ttcaacatta atagcagcct tctctctat                 2702

<210> SEQ ID NO 4
<211> LENGTH: 781
<212> TYPE: PRT
<213> ORGANISM: Mus musculus

<400> SEQUENCE: 4

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160
```

-continued

```
Asn Asp Glu Asp Gln Val Val Asn Lys Ala Ala Val Met Val His
            165                 170                 175
Gln Leu Ser Lys Lys Glu Ala Ser Arg His Ala Ile Met Arg Ser Pro
        180                 185                 190
Gln Met Val Ser Ala Ile Val Arg Thr Met Gln Asn Thr Asn Asp Val
    195                 200                 205
Glu Thr Ala Arg Cys Thr Ala Gly Thr Leu His Asn Leu Ser His His
210                 215                 220
Arg Glu Gly Leu Leu Ala Ile Phe Lys Ser Gly Ile Pro Ala Leu
225                 230                 235                 240
Val Lys Met Leu Gly Ser Pro Val Asp Ser Val Leu Phe Tyr Ala Ile
                245                 250                 255
Thr Thr Leu His Asn Leu Leu His Gln Gly Ala Lys Met Ala
            260                 265                 270
Val Arg Leu Ala Gly Gly Leu Gln Lys Met Val Ala Leu Leu Asn Lys
        275                 280                 285
Thr Asn Val Lys Phe Leu Ala Ile Thr Thr Asp Cys Leu Gln Ile Leu
    290                 295                 300
Ala Tyr Gly Asn Gln Glu Ser Lys Leu Ile Ile Leu Ala Ser Gly Gly
305                 310                 315                 320
Pro Gln Ala Leu Val Asn Ile Met Arg Thr Tyr Thr Tyr Glu Lys Leu
                325                 330                 335
Leu Trp Thr Thr Ser Arg Val Leu Lys Val Leu Ser Val Cys Ser Ser
            340                 345                 350
Asn Lys Pro Ala Ile Val Glu Ala Gly Gly Met Gln Ala Leu Gly Leu
        355                 360                 365
His Leu Thr Asp Pro Ser Gln Arg Leu Val Gln Asn Cys Leu Trp Thr
    370                 375                 380
Leu Arg Asn Leu Ser Asp Ala Ala Thr Lys Gln Glu Gly Met Glu Gly
385                 390                 395                 400
Leu Leu Gly Thr Leu Val Gln Leu Leu Gly Ser Asp Asp Ile Asn Val
                405                 410                 415
Val Thr Cys Ala Ala Gly Ile Leu Ser Asn Leu Thr Cys Asn Asn Tyr
            420                 425                 430
Lys Asn Lys Met Met Val Cys Gln Val Gly Gly Ile Glu Ala Leu Val
        435                 440                 445
Arg Thr Val Leu Arg Ala Gly Asp Arg Glu Asp Ile Thr Glu Pro Ala
    450                 455                 460
Ile Cys Ala Leu Arg His Leu Thr Ser Arg His Gln Glu Ala Glu Met
465                 470                 475                 480
Ala Gln Asn Ala Val Arg Leu His Tyr Gly Leu Pro Val Val Val Lys
                485                 490                 495
Leu Leu His Pro Pro Ser His Trp Pro Leu Ile Lys Ala Thr Val Gly
            500                 505                 510
Leu Ile Arg Asn Leu Ala Leu Cys Pro Ala Asn His Ala Pro Leu Arg
        515                 520                 525
Glu Gln Gly Ala Ile Pro Arg Leu Val Gln Leu Leu Val Arg Ala His
    530                 535                 540
Gln Asp Thr Gln Arg Arg Thr Ser Met Gly Gly Thr Gln Gln Gln Phe
545                 550                 555                 560
Val Glu Gly Val Arg Met Glu Glu Ile Val Glu Gly Cys Thr Gly Ala
                565                 570                 575
```

-continued

```
Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
                660                 665                 670

Arg Leu Ser Val Glu Leu Thr Ser Ser Leu Phe Arg Thr Glu Pro Met
            675                 680                 685

Ala Trp Asn Glu Thr Ala Asp Leu Gly Leu Asp Ile Gly Ala Gln Gly
        690                 695                 700

Glu Ala Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
                740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
770                 775                 780
```

USE OF β-CATENIN IN THE EXPANSION OF STEM AND PROGENITOR CELLS

CROSS-REFERENCE TO RELATED APPLICATIONS

This application clams priority of U.S. provisional patent application 60/176,786, filed Jan. 18, 2000.

Beta-catenin is a pivotal player in the signaling pathway initiated by Wnt proteins, which are mediators of several developmental processes. Beta-catenin activity is controlled by a large number of binding partners that affect the stability and the localization of beta-catenin, and it is thereby able to participate in such varying processes as gene expression and cell adhesion. Activating mutations in beta-catenin and in components regulating its stability have been found to contribute to upregulation of cell proliferation.

The β-catenin protein becomes stabilized in response to Wnt/Wg, moves to the nucleus and forms complexes with the LEF1/TCF transcription factors to regulate gene expression. The level of cytosolic β-catenin is determined by its interaction with a number of proteins including those in a multiprotein complex of Axin, GSK-3β, APC and other proteins. The mechanism by which the Wnt signal is transmitted to this complex is unclear but it involves interaction of Wnt with its receptors, which are members of Frizzled family of seven transmembrane proteins. The stabilization of β-catenin stimulates the expression of genes including c-myc, c-jun, fra-1, and cyclin D1. This pathway is negatively regulated by Axin.

Beta-catenin is also an adherens junction protein. Adherens junctions are critical for the establishment and maintenance of epithelial layers, such as those lining organ surfaces. AJs mediate adhesion between cells, communicate a signal that neighboring cells are present, and anchor the actin cytoskeleton. In serving these roles, AJs regulate normal cell growth and behavior. At several stages of embryogenesis, wound healing, and tumor cell metastasis, cells form and leave epithelia. This process, which involves the disruption and reestablishment of epithelial cell—cell contacts, may be regulated by the disassembly and assembly of AJs. AJs may also function in the transmission of the 'contact inhibition' signal, which instructs cells to stop dividing once an epithelial sheet is complete.

For many purposes, there is an interest in being able to expand stem and progenitor cells in culture. However, it is not simply a matter of maintaining cell viability for the stem cells, but also of ensuring that the stem cells increase in numbers without losing their distinctive phenotype. Current protocols for the in vitro culture of hematopoietic stem cells generally require one or a cocktail of cytokines, such as c-kit ligand (stem cell growth factor), flt-3, thrombopoietin, IL-6, etc. While a substantial increase in cell number can be obtained with such cultures, they do not provide for expanded number of cells that retain a capacity for long term repopulation of all hematopoietic lineages. See Domen and Weissman (1999) Mol Med Today 5(5):201-8; or Ziegler and Kanz (1998) Curr Opin Hematol 5(6):434-40.

Stem cells have also been grown in co-culture with stromal cells. However, it is particularly desirable to expand stem cells in a culture of known composition, rather than relying upon the presence of other cells for their maintenance.

There continues to be a strong demand for improvements in the in vitro culture of stem cells and progenitor cells. The present invention addresses this need.

SUMMARY OF THE INVENTION

Methods are provided for the expansion of progenitor or stem cells in vitro, whereby the cells retain their pluripotential phenotype after expansion. The intracellular level of β-catenin is increased in the cells in culture, either by providing exogenous β-catenin protein to the cell, or by introduction into the cell of a genetic construct encoding β-catenin. The β-catenin may be a wild type protein appropriate for the species from which the cells are derived, or preferably, a stabilized mutant form of the protein. The alteration in cellular levels of β-catenin provide for increased number of cells in cycle, and leads to cultures that containing proliferating cells that maintain an undifferentiated phenotype in vitro. The expanded cell populations are useful as a source of stem cells, e.g. to reconstitute function in a host that is deficient in a particular cell lineage or lineages. In one embodiment of the invention, the target cells are hematopoietic stem cells, which may be used in transplantation to restore hematopoietic function to autologous or allogeneic recipients.

DESCRIPTION OF THE SPECIFIC EMBODIMENTS

Figure 1:
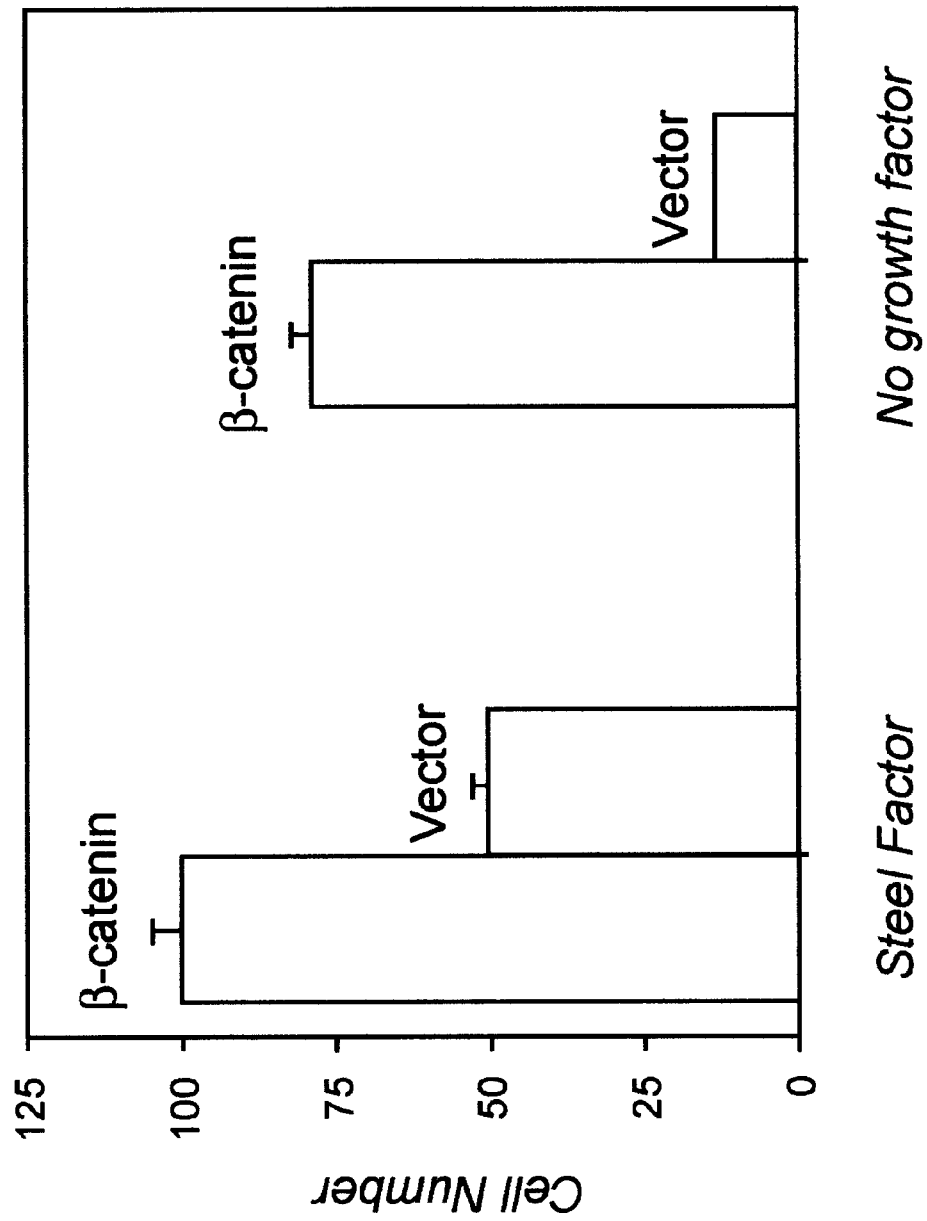
FIG. 1. Activated beta-catenin retrovirus induces increased growth of stem cells. Stem cells infected with control or beta-catenin-GFP retrovirus were sorted and cultured on 96 well plates for two days in the presence or absence of steel factor, and cell numbers were counted at the end of the culture period.
Figure 2A:
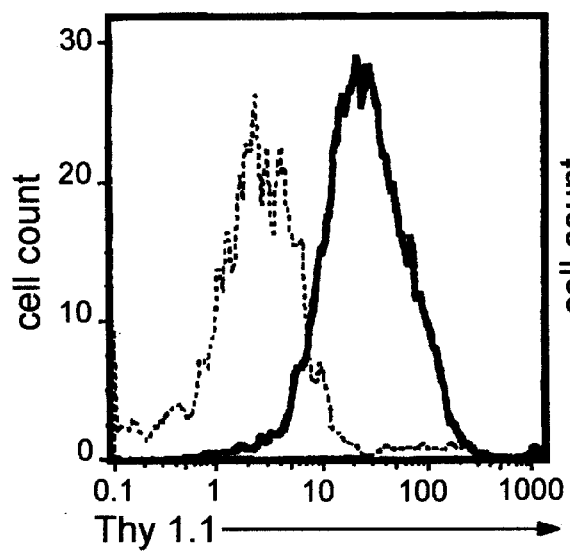
FIGS. 2A, B, C, D. Stem cells infected with beta-catenin retain many stem cell markers in long term culture. Beta-catenin infected stem cell spheres were harvested from long tem cultures at 5 weeks, trypsinized and allowed to express their surface proteins for 12 hours. Subsequently they were harvested and stained with antibodies to Thy1.1, Sca1, c-kit, and lineage antigens (B220, Mac-1, Gr-1, Ter119, CD5, CD3, CD8/4).
Figure 2B:
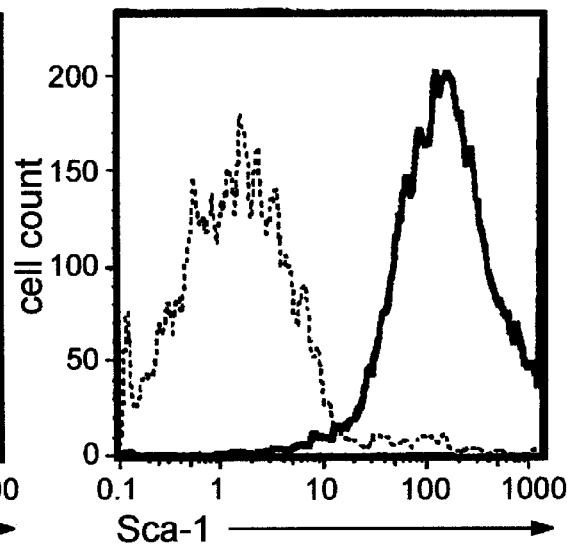
Figure 2C:
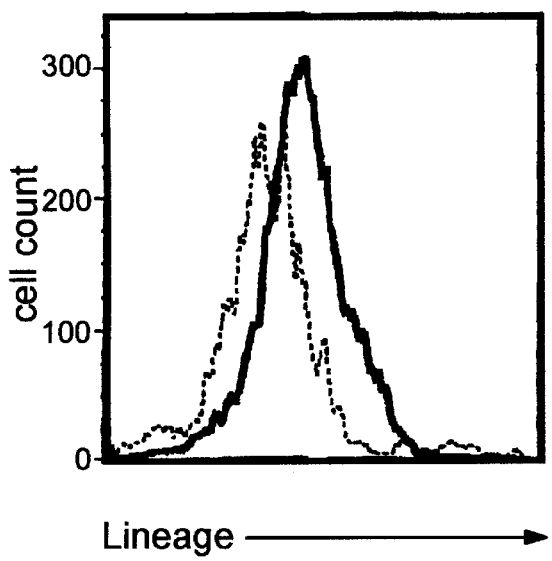
Figure 2D:
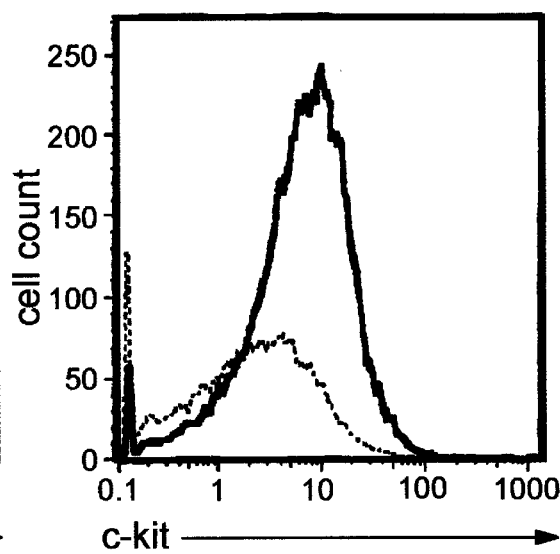
Figure 3A:
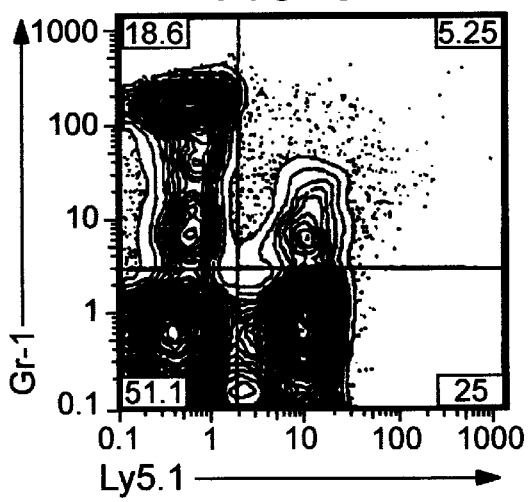
FIGS. 3A, B, C, D, E. Stem cells infected with beta-catenin have the ability to give rise to multiple lineages when transplanted. 100,000 beta-catenin infected stem cells were harvested from long term cultures at 7 weeks, trypsinized and injected into lethally irradiated (950 Rads) allotype marked recipients along with 300,000 rescuing bone marrow cells from the host. Analysis of reconstitution along various lineages was carried out at 4 weeks after transplantation.
Figure 3B:
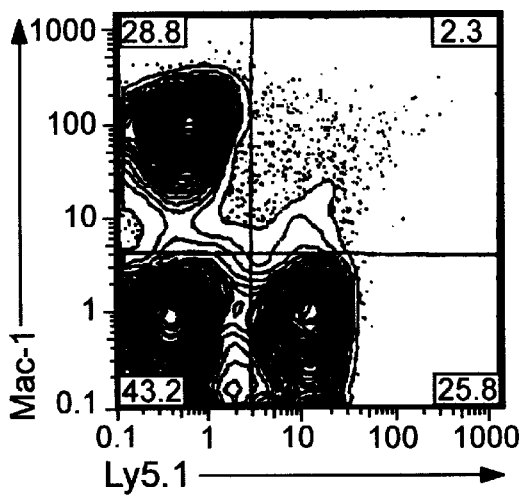
Figure 3C:
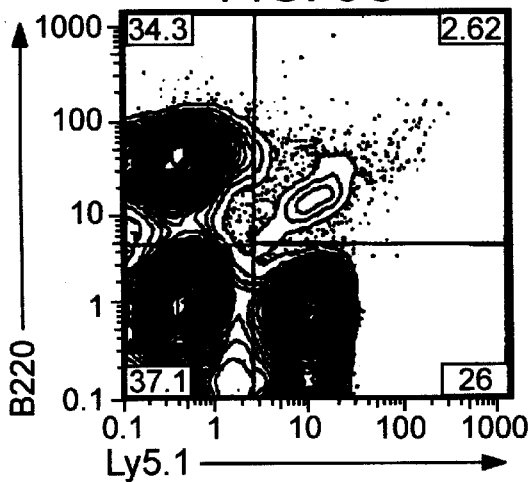
Figure 3D:
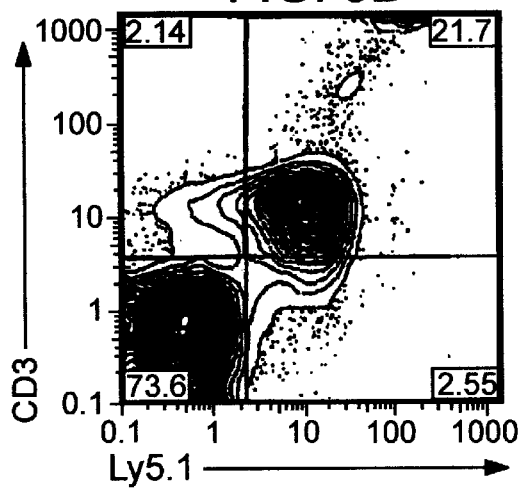
Figure 3E:
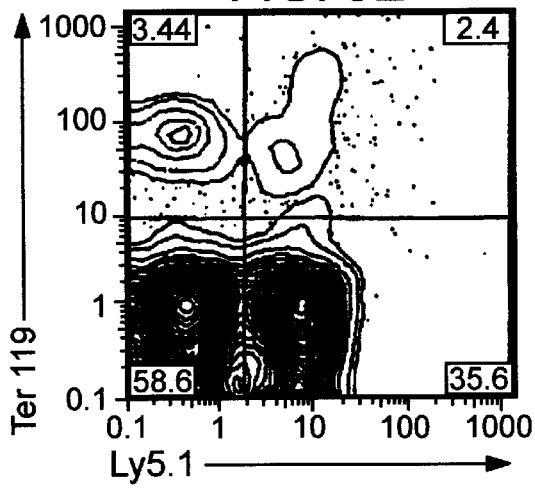

Mammalian progenitor or stem cells are expanded in vitro by increasing the levels of β-catenin in the cell. The intracellular levels of β-catenin may be manipulated by providing exogenous β-catenin protein to the cell, or by introduction into the cell of a genetic construct encoding β-catenin. The β-catenin may be a wild-type or stabilized mutant form of the protein. Preferably the long term cell culture medium substantially lacks stromal cells and cytokines. Cultures that provide stem cell activity can be obtained for at least three weeks, frequently six weeks and can be eight weeks or more. The culture media that are employed are conventional media for the growth of mammalian cells, optionally in the absence of serum using only defined protein factors. In the absence of the β-catenin, the medium is inefficient at maintaining growth of the undifferentiated cells.

In the first few days of culture, the expansion of stem/progenitor cells is limited, usually the number of phenotypic stem/progenitor cells is maintained, or slightly increased. After 2 to 3 weeks in the subject culture conditions, there is a substantial proliferation of cells having the desired phenotype, where the number of cells having a functional stem/progenitor cell phenotype is expanded.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

β-catenin

The term β-catenin, as used herein, is intended to refer to both wild-type and stabilized forms of the β-catenin protein, and to fusion proteins and derivatives thereof. Usually the protein will be of mammalian origin, although the protein from other species may find use. The protein is conserved between species, for example the human sequence is active in mouse cells. The sequences of many β-catenin proteins are publicly known. For convenience, the sequences of the human and mouse homologs of this protein are provided in the sequence listing, as SEQ ID NO:1; and SEQ ID NO:2, respectively. In one embodiment of the invention, a stabilized form of beta-catenin is used.

The ubiquitin-dependent proteolysis system is involved in the regulation of beta-catenin turnover. Beta-catenin becomes stabilized when proteasome-mediated proteolysis is inhibited and this leads to the accumulation of multi-ubiquitinated forms of beta-catenin (Aberle et al. (1997) EMBO J 16(13):3797-804). Substitution of the serine residues in the glycogen synthase kinase 3β (GSK3beta) phosphorylation consensus motif of beta-catenin inhibits ubiquitination and results in stabilization of the protein. Examples of stabilized β-catenins include those with the amino acid changes D32Y; D32G; S33F; S33Y; G34E; S37C; S37F; T41I; S45Y; and deletion of AA 1–173. A number of publications describe stabilized β-catenin mutations. For example, see Morin et al. (1997) Science 275 (5307):1787-90; Palacios et al. (1998) Cancer Res 58(7):1344-7; Muller et al. (1998) Genes Chromosomes Cancer 22(1):37–41; Miyoshi et al. (1998) Cancer Res 58(12):2524-7; Zurawel et al. (1998) Cancer Res. 58, 896–899; Voeller et al. (1998) Cancer Res. 58, 2520–2526; etc.

The sequence of the beta-catenin polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. Deletions may further include larger changes, such as deletions of a domain or exon, providing for active peptide fragments of the protein. Other modifications of interest include tagging, e.g. with the FLAG system, HA, green fluorescent protein, etc. Such alterations may be used to alter properties of the protein, by affecting the stability, specificity, etc. The protein may be joined to a wide variety of other oligopeptides or proteins for a variety of purposes, particular for facilitating transport across membranes.

Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3–15.108; Weiner et al., Gene 126:35–41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67–70 (1989); and Zhu Anal Biochem 177:120-4 (1989).

Expression Construct

In one embodiment of the invention, the beta-catenin is delivered to the targeted stem or progenitor cells by introduction of an exogenous nucleic acid expression vector into the cells. Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc.

Retrovirus based vectors have been shown to be particularly useful when the target cells are hematopoietic stem cells. For example, see Baum et al. (1996) J Hematother 5(4):323-9; Schwarzenberger et al. (1996) Blood 87:472–478; Nolta et al. (1996) P.N.A.S. 93:2414–2419; and Maze et al. (1996) P.N.A.S. 93:206–210. Lentivirus vectors have also been described for use with hematopoietic stem cells, for example see Mochizuki et al. (1998) J Virol 72(11):8873-83. The use of adenovirus based vectors with hematopoietic cells has also been published, see Ogniben and Haas (1998) Recent Results Cancer Res 144:86–92.

Various techniques known in the art may be used to transfect the target cells, e.g. electroporation, calcium precipitated DNA, fusion, transfection, lipofection and the like. The particular manner in which the DNA is introduced is not critical to the practice of the invention.

Combinations of retroviruses and an appropriate packaging line may be used, where the capsid proteins will be functional for infecting the target cells. Usually, the cells and virus will be incubated for at least about 24 hours in the culture medium. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392–8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431–437); PA317 (Miller et al. (1986) Mol. Cell. Biol. 6:2895–2902) GRIP (Danos et al. (1988) PNAS 85:6460–6464). Retroviruses packaged with xenotropic envelope protein, e.g. AKR env, are capable of infecting most mammalian cell types, except murine cells.

The sequences at the 5' and 3' termini of the retrovirus are long terminal repeats (LTR). A number of LTR sequences are known in the art and may be used, including the MMLV-LTR; HIV-LTR; AKR-LTR; FIV-LTR; ALV-LTR; etc. Specific sequences may be accessed through public databases. Various modifications of the native LTR sequences are also known. The 5' LTR acts as a strong promoter, driving transcription of the β-catenin gene after integration into a target cell genome. For some uses, however, it is desirable to have a regulatable promoter driving expression. Where such a promoter is included, the promoter function of the LTR will be inactivated. This is accomplished by a deletion of the U3 region in the 3' LTR, including the enhancer repeats and promoter, that is sufficient to inactivate the promoter function. After integration into a target cell genome, there is a rearrangement of the 5' and 3' LTR, resulting in a transcriptionally defective provirus, termed a "self-inactivating vector".

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in hematopoietic cell types, e.g. IL-2 promoter in T cells, immunoglobulin promoter in B cells, etc.

Preferred genetic constructs are those that can be removed from the target cells after expansion. This can be accomplished by the use of a transient vector system, or by including a heterologous recombination site that flanks the beta-catenin coding sequence. In this manner, after expansion the construct can be removed prior to use of the expanded cell population. Preferably a detectable marker, e.g. green fluorescent protein, luciferase, cell surface proteins suitable for antibody selection methods, etc. is included in the expression vector, such that after deletion of the construct the cells can be readily isolated that lack the exogenous beta-catenin.

The term "heterologous recombination site" is meant to encompass any introduced genetic sequence that facilitates site-specific recombination. In general, such sites facilitate recombination by interaction of a specific enzyme with two such sites. Exemplary heterologous recombination sites include, but are not necessarily limited to, lox sequences with recombination mediated by Cre enzyme; frt sequences (Golic et al. (1989) Cell 59:499–509; O'Gorman et al. (1991) Science 251:1351-5; recombination mediated by the FLP recombinase), the recognition sequences for the pSR1 recombinase of Zygosaccharomyces rouxii (Matsuzaki et al. (1990) J. Bacteriol. 172:610-8), and the like.

Sequences encoding lox sites are of particular interest for use in the present invention. A lox site is a nucleotide sequence at which the gene product of the cre gene, referred to herein as "Cre," catalyzes site-specific recombination. A particularly preferred lox site is a loxP site. The sequence of loxP, which is 34 bp in length, is known and can be produced synthetically or can be isolated from bacteriophage P1 by methods known in the art (see, e.g. Hoess et al. (1982) Proc. Natl. Acad. Sci. USA 79:3398). The loxP site is composed of two 13 bp inverted repeats separated by an 8 bp spacer region. Other suitable lox sites include loxB, loxL, and loxR, which can be isolated from E. coli (Hoess et al. (1982) Proc. Natl. Acad. Sci. USA 22:3398).

In an alternative method, expression vectors that provide for the transient expression in mammalian cells may be used. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient short term expansion of cells, but do not affect the long term genotype of the cell.

Translocation Modified β-catenin

In some cases it is desirable to provide exogenous β-catenin protein, rather than transducing the cells with an expression construct. The beta-catenin may be added to the culture medium at high levels. Preferably the beta-catenin is modified so as to increase its transport into the cells.

In one embodiment of the invention, tat protein is used to deliver beta-catenin. The preferred transport polypeptides are characterized by the presence of the tat basic region amino acid sequence (amino acids 49–57 of naturally-occurring tat protein); the absence of the tat cysteine-rich region amino acid sequence (amino acids 22–36 of naturally-occurring tat protein) and the absence of the tat exon 2-encoded carboxy-terminal domain (amino acids 73–86 of naturally-occurring tat protein). Transport polypeptides are attached to beta-catenin by chemical cross-linking or by genetic fusion, where the beta-catenin moiety may be a wild-type or stabilized form. A unique terminal cysteine residue is a preferred means of chemical cross-linking.

Stem Cell

The term stem cell is used herein to refer to a mammalian cell that has the ability both to self-renew, and to generate differentiated progeny (see Morrison et al. (1997) Cell 88:287–298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Stem cells may be characterized by both the presence of markers associated with specific epitopes identified by antibodies and the absence of certain markers as identified by the lack of binding of specific antibodies. Stem cells may also be identified by functional assays both in vitro and in vivo, particularly assays relating to the ability of stem cells to give rise to multiple differentiated progeny.

Stem cells of interest include hematopoietic stem cells and progenitor cells derived therefrom (U.S. Pat. No. 5,061, 620); neural crest stem cells (see Morrison et al. (1999) Cell 96:737–749); embryonic stem cells; mesenchymal stem cells; mesodermal stem cells; etc.

Other hematopoietic "progenitor" cells of interest include cells dedicated to lymphoid lineages, e.g. immature T cell and B cell populations. The methods of the present invention are useful in expanding selected populations of these cells.

Purified populations of stem or progenitor cells may be used to initiate the cultures. For example, human hematopoietic stem cells may be positively selected using antibodies specific for CD34, thy-1; or negatively selected using lineage specific markers which may include glycophorin A, CD3, CD24, CD16, CD14, CD38, CD45RA, CD36, CD2, CD19, CD56, CD66a, and CD66b; T cell specific markers, tumor specific markers, etc. Markers useful for the separation of mesodermal stem cells include FcγRII, FcγRIII, Thy-1, CD44, VLA-4α, LFA-1β, HSA, ICAM-1, CD45, Aa4.1, Sca-1, etc. Neural crest stem cells may be positively selected with antibodies specific for low-affinity nerve growth factor receptor (LNGFR), and negatively selected for the markers sulfatide, glial fibrillary acidic protein (GFAP), myelin protein $P_o$, peripherin and neurofilament. Human mesenchymal stem cells may be positively separated using the markers SH2, SH3 and SH4.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

The cells which are employed may be fresh, frozen, or have been subject to prior culture. They may be fetal, neonate, adult. Hematopoietic cells may be obtained from fetal liver, bone marrow, blood, particularly G-CSF or GM-CSF mobilized peripheral blood, or any other conventional source. The manner in which the stem cells are separated from other cells of the hematopoietic or other lineage is not critical to this invention. As described above, a substantially homogeneous population of stem or progenitor cells may be obtained by selective isolation of cells free of markers associated with differentiated cells, while displaying epitopic characteristics associated with the stem cells.

Culture Medium

The stem or progenitor cells are grown in vitro in an appropriate liquid nutrient medium. Generally, the seeding level will be at least about 10 cells/ml, more usually at least about 100 cells/ml and generally not more than about $10^5$ cells/ml, usually not more than about $10^4$ cells/ml.

Various media are commercially available and may be used, including Ex vivo serum free medium; Dulbecco's Modified Eagle Medium (DMEM), RPMI, Iscove's medium, etc. The medium may be supplemented with serum or with defined additives. Appropriate antibiotics to prevent bacterial growth and other additives, such as pyruvate (0.1–5 mM), glutamine (0.5–5 mM), 2-mercaptoethanol (1–10× $10^{-5}$ M) may also be included.

Culture in serum-free medium is of particular interest. The medium may be any conventional culture medium, generally supplemented with additives such as iron-saturated transferrin, human serum albumin, soy bean lipids, linoleic acid, cholesterol, alpha thioglycerol, crystalline bovine hemin, etc., that allow for the growth of hematopoietic cells.

Preferably the expansion medium is free of cytokines, particularly cytokines that induce cellular differentiation. The term cytokine may include lymphokines, monokines and growth factors. Included among the cytokines are thrombopoietin (TPO); nerve growth factors such as NGF-.beta.; platelet-growth factor; transforming growth factors (TGFs) such as TGF-α and TGF-β; erythropoietin (EPO); interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; etc. In some circumstances, proliferative factors that do not induce cellular differentiation may be included in the cultures, e.g. c-kit ligand, LIF, and the like.

Expansion of Stem/Progenitor Cells

A population of cells comprising progenitor and/or stem cells is cultured in vitro in the presence of enhanced levels of β-catenin, either by genetically altering the cells, or by providing exogenous β-catenin, as described above. The upregulation in β-catenin is sufficient to maintain or increase the number of assayable progenitor cells in the culture. The number of assayable progenitor cells may be demonstrated by a number of assays. After one week the progenitor cell cloning efficiency will usually be at least about 75% that of the starting cell population, more usually 100% that of the starting cell population, and may be as high as 200% that of the starting cell population.

Following the initial period, there is an increased expansion, where the number of assayable cells having the functional phenotype of the initial cell population can increase from about 5 to about 100 fold or more. After this time, the cells can remain in cycle, and expansion is limited primarily by considerations of space. The cells can be frozen using conventional methods at any time, usually after the first week of culture.

Frequently stem cells are isolated from biological sources in a quiescent state. Certain expression vectors, particularly retroviral vectors, do not effectively infect non-cycling cells. Cultures established with these vectors as a source of beta-catenin sequences are induced to enter the cell cycle by a short period of time in culture with growth factors. For example, hematopoietic stem cells are induced to divide by culture with c-kit ligand, which may be combined with LIF, IL-11 and thrombopoietin. After 24 to 72 hours in culture with cytokines, the medium is changed, and the cells are contacted with the retroviral culture, using culture conditions as described above.

After seeding the culture medium, the culture medium is maintained under conventional conditions for growth of mammalian cells, generally about 37° C. and 5% $CO_2$ in 100% humidified atmosphere. Fresh media may be conveniently replaced, in part, by removing a portion of the media and replacing it with fresh media. Various commercially available systems have been developed for the growth of mammalian cells to provide for removal of adverse metabolic products, replenishment of nutrients, and maintenance of oxygen. By employing these systems, the medium may be maintained as a continuous medium, so that the concentrations of the various ingredients are maintained relatively constant or within a predescribed range. Such systems can provide for enhanced maintenance and growth of the subject cells using the designated media and additives.

These cells may find various applications for a wide variety of purposes. The cell populations may be used for screening various additives for their effect on growth and the mature differentiation of the cells. In this manner, compounds which are complementary, agonistic, antagonistic or inactive may be screened, determining the effect of the compound in relationship with one or more of the different cytokines.

The populations may be employed as grafts for transplantation. For example, hematopoietic cells are used to treat malignancies, bone marrow failure states and congenital metabolic, immunologic and hematologic disorders. Marrow samples may be taken from patients with cancer, and enriched populations of hematopoietic stem cells isolated by means of density centrifugation, counterflow centrifugal elutriation, monoclonal antibody labeling and fluorescence activated cell sorting. The stem cells in this cell population are then expanded in vitro and can serve as a graft for autologous marrow transplantation. The graft will be infused after the patient has received curative chemo-radiotherapy.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Experimental

Bone marrow cells from BCI2 transgenic mice were isolated, enriched for c-kit over a magnetic column, and then stained with antibodies to sort the Sca1+ Thy1.1$^{lo}$ c-kit$^+$ lin$^{-/lo}$ population on a cell sorter. The cells were double sorted to ensure a high level of purity.

The cells were cultured to initiate cell cycle with Steel factor 100 ng/ml with 5% serum in X-Vivo 15 containing the retrovirus. At 3 days 50% of media was replaced with only X-vivo 15, and this dilution was repeated every 2 days. The cells were then cultured with supernatant containing retrovirus encoding activated beta-catenin and recombinant steel factor. The increased growth of the stem cells is shown in FIG. 1.

The retroviral supernatant had been generated in commercially available X-vivo 15 media using phoenix cells and a MSCV retroviral construct containing beta-catenin driven by the LTR. The retroviral construct is called MSCV and contains an IRES-GFP, in order to label infected cells. The activating beta catenin mutation is a mutation at the amino terminus that prevents phosphorylation and subsequent degradation by proteosomes. The accumulation of beta catenin in the cytosol allows it to translocate to the nucleus where it associates with the LEF/TCF family of transcription factors to turn on gene expression.

50% of the culture supernatant was replaced every day for 3 days. At the end of this culture period the media was replaced with X-vivo 15. Clusters of cells grew out of this culture, and were analyzed at 5 weeks. By May-Gruenwald-Geimsa staining, these cells appeared to have an immature phenotype with large nuclei and small cytoplasm. By FACS staining a majority of cells are Thy1$^{lo}$ Sca-1$^+$Lin$^{lo/-}$kit$^{lo}$, a phenotype resembling that of stem cells. About 50% of the cells are Lin-(LT-HSC phenotype), and 50% Lin$^{lo}$ (ST-HSC phenotype). The analysis is shown in FIG. 2.

These cells give rise to lineage positive cells at 4 weeks when transplanted into lethally irradiated mice suggesting that they are able to differentiate to various lineages in vivo, while remaining immature in vitro.

Lethally irradiated mice were injected with 300, 000 host bone marrow and 100,000 cultured cells. Peripheral blood was take at a later time, at 2 weeks, 3 weeks and 4 weeks so far. Donor type was marked with Ly5.1+ cells. Level of differentiation was determined by using antibodies to mature lineage markers. The results are shown in FIG. 3, demonstrating that stem cells over-expressing β-catenin have the ability to give rise to multiple lineages when transplanted.

What is claimed is:

1. A method for in vitro self-renewal of mammalian stem cells, the method comprising: transfecting said stem cells in an in vitro culture medium with an exogenous nucleic acid comprising stabilized mutant β-catenin coding sequences operably linked to a promoter, culturing said stem cells for a period of time sufficient for said cells to divide and self-renew, wherein the intracellular concentration of β-catenin is increased compared to untransfected cells, whereby the number of cells having the ability to self-renew and to generate differential progeny in multiple lineages when implanted into an animal is expanded compared to untransfected cells.

2. The method of claim 1, wherein said stem cell has the ability to undergo asynchronous replication; has extensive self-renewal capacity; and has the capacity for existence in a mitotically quiescent form.

3. The method of claim 2, wherein said stem cell is a hematopoietic stem cell.

4. The method of claim 2, wherein said stem cell is a neural crest stem cell.

5. The method of claim 2, wherein said stem cell is a mesenchymal stem cell.

6. The method of claim 2, wherein said stem cell is an embryonic stem cell.

7. The method of claim 3, wherein said hematopoietic stem cell is a human cell.

8. The method of claim 1, wherein said exogenous nucleic acid is a retroviral vector.

9. The method of claim 8, wherein said retroviral vector comprises sites for recombination, flanking said beta-catenin coding sequences.

10. The method of claim 1, wherein said exogenous nucleic acid is an episomal vector.

11. A method for in vitro self-renewal of mammalian stem cells, the method comprising: treating said stem cells by addition of an exogenous stabilized mutant β-catenin to the culture medium, culturing said stem cells for a period of time sufficient for said cells to divide and self-renew, wherein the intracellular concentration of β-catenin is increased compared to untreated cells, whereby the number of cells having the ability to self-renew and to generate differentiated progeny in multiple lineages when implanted into an animal is expanded compared to untreated cells.

12. The method of claim 11, wherein said beta-catenin is genetically fused to a transport moiety.

13. The method of claim 12, wherein said transport moiety is a fragment of HIV tat protein.

14. A method for in vitro self-renewal of mammalian hematopoietic stem cells, the method comprising: transfecting said stem cells in an in vitro culture medium with an exogenous nucleic acid comprising stabilized mutant β-catenin coding sequences operably linked to a promoter, culturing the stem cells for a period of time sufficient for said cells to divide and self-renew, wherein the intracellular concentration of β-catenin is increased compared to untransfected cells, whereby the number of cells having the ability to self-renew and to generate differentiated progeny in multiple lineages when implanted into an animal is expanded compared to untransfected cells.

15. The method according to claim 14, wherein said hematopoietic stem cells are mouse hematopoietic stem cells.

16. The method according to claim 14, wherein said hematopoietic stem cells are human hematopoietic stem cells.

17. The method according to claim 16, wherein said human hematopoietic stem cells are CD34 positive, thy-1positive, and lineage negative.

* * * * *

UNITED STATES PATENT AND TRADEMARK OFFICE
CERTIFICATE OF CORRECTION

PATENT NO. : 6,465,249 B2
DATED : October 15, 2002
INVENTOR(S) : Reya, Tannishtha et al.

It is certified that error appears in the above-identified patent and that said Letters Patent is hereby corrected as shown below:

Column 1,
Line 5, after "CROSS-REFERENCE TO RELATED APPLICATIONS" please insert the following:
-- This invention was made with Government support under contract CA 42551 awarded by the NIH National Cancer Institute. The Government has certain rights in this invention. --

Signed and Sealed this

Twenty-fifth Day of March, 2003

JAMES E. ROGAN
*Director of the United States Patent and Trademark Office*